(12) United States Patent
Salomir et al.

(10) Patent No.: US 8,583,211 B2
(45) Date of Patent: Nov. 12, 2013

(54) METHOD FOR TEMPERATURE CONTROL IN MAGNETIC RESONANCE-GUIDED VOLUMETRIC ULTRASOUND THERAPY

(75) Inventors: Rares Salomir, Evires (FR); Magalie Viallon, Lyons (FR)

(73) Assignee: Siemens Aktiengesellschaft, Munich (DE)

( * ) Notice: Subject to any disclaimer, the term of this patent is extended or adjusted under 35 U.S.C. 154(b) by 137 days.

(21) Appl. No.: 13/206,867

(22) Filed: Aug. 10, 2011

(65) Prior Publication Data
US 2013/0041249 A1 Feb. 14, 2013

(51) Int. Cl.
*A61B 5/055* (2006.01)

(52) U.S. Cl.
USPC .............. 600/411; 600/412; 600/439

(58) Field of Classification Search
None
See application file for complete search history.

(56) References Cited

U.S. PATENT DOCUMENTS

| | | | | |
|---|---|---|---|---|
| 6,128,522 A * | 10/2000 | Acker et al. | ........... | 600/411 |
| 6,188,923 B1 * | 2/2001 | Bechtold | ........... | 600/427 |
| 6,823,216 B1 * | 11/2004 | Salomir et al. | ........... | 607/101 |
| 7,792,566 B2 * | 9/2010 | Roland et al. | ........... | 600/411 |
| 8,088,067 B2 * | 1/2012 | Vortman et al. | ........... | 600/437 |
| 8,335,554 B2 * | 12/2012 | Pananakis et al. | ........... | 600/411 |
| 2004/0039280 A1 * | 2/2004 | Wu et al. | ........... | 600/412 |
| 2006/0206105 A1 * | 9/2006 | Chopra et al. | ........... | 606/27 |
| 2007/0167705 A1 * | 7/2007 | Chiang et al. | ........... | 600/407 |
| 2007/0238976 A1 * | 10/2007 | Ishihara | ........... | 600/411 |
| 2008/0058634 A1 * | 3/2008 | Roland et al. | ........... | 600/411 |
| 2008/0114274 A1 * | 5/2008 | Moonen et al. | ........... | 601/3 |
| 2008/0146912 A1 * | 6/2008 | Richard et al. | ........... | 600/411 |
| 2008/0194941 A1 * | 8/2008 | Steinmeyer et al. | ........... | 600/411 |
| 2008/0275330 A1 * | 11/2008 | Mu et al. | ........... | 600/411 |
| 2009/0012514 A1 * | 1/2009 | Moonen et al. | ........... | 606/27 |
| 2009/0093708 A1 * | 4/2009 | Wang et al. | ........... | 600/411 |
| 2009/0192383 A1 * | 7/2009 | Pananakis et al. | ........... | 600/411 |
| 2009/0221902 A1 * | 9/2009 | Myhr | ........... | 600/411 |
| 2010/0217114 A1 * | 8/2010 | Zhou et al. | ........... | 600/411 |
| 2010/0280356 A1 * | 11/2010 | Kohler et al. | ........... | 600/411 |
| 2011/0046472 A1 * | 2/2011 | Schmidt et al. | ........... | 600/411 |
| 2011/0137147 A1 * | 6/2011 | Skliar et al. | ........... | 600/411 |
| 2012/0083686 A1 * | 4/2012 | Virta et al. | ........... | 600/411 |
| 2012/0296197 A1 * | 11/2012 | Vahala et al. | ........... | 600/411 |

FOREIGN PATENT DOCUMENTS

WO WO 2007047247 A1 * 4/2007

OTHER PUBLICATIONS

Salomir et al., "Hyperthermia by MR-Guided Focused Ultrasound: Accurate Temperature Control Based on Fast MRI and a Physical Modal of Local Energy Deposition and Heat Conduction," Magnetic Resonance in Medicine, vol. 43 (2000), pp. 342-347.

(Continued)

*Primary Examiner* — Jonathan G Cwern
*Assistant Examiner* — Amelie R Gillman
(74) *Attorney, Agent, or Firm* — Schiff Hardin LLP (57) ABSTRACT

In a method for temperature control in MR-guided administration of ultrasound, ultrasound therapy is administered to a patient at an in vivo site by emitting focused ultrasound into the site at multiple foci with a multi-focus ultrasound therapy device. The temperature is monitored in a localized region of an examination subject in which the site is located during the therapy in real-time by MR thermometry. From the MR thermometry, characteristics of the temperature distribution in the monitored region of the examination subject are automatically identified. Temperature control is implemented by regulating the energy output of the ultrasound therapy device, according to a rapidly converging master equation.

5 Claims, 10 Drawing Sheets

(56) References Cited

OTHER PUBLICATIONS

Mougenot et al., "Automatic Spatial and Temporal Temperature Control for MR-Guided Focused Ultrasound Using Fast 3D MR Thermometry and Multispiral Trajectory of the Focal Point," Magnetic Resonance in Medicine, vol. 52 (2004), pp. 1005-1015.

Mougenot et al., "Three-Dimensional Spatial and Temporal Temperature Control With MR Thermometry-Guided Focused Ultrasound (MRgH1FU)," Magnetic Resonance in Medicine, vol. 61 (2009), pp. 603-614.

Salomir et al., "Endocavitary thermal therapy by MRI-guided phased-array contact ultrasound: Experimental and numerical studies on the multi-input single-output PID temperature controller's convergence and stability," Med. Phys., vol. 36 (10) (2009), pp. 4726-4741.

Ross et al., "Curvilinear transurethral ultrasound applicator for selective prostate thermal therapy," Med. Phys., vol. 32 (6) (2005), pp. 1555-1565.

Arora, D. et al., "Control of thermal therapies with moving power deposition field," Institute of Physics Publishing, Phys. Med. Biol., vol. 51 (2008), pp. 1201-1219.

* cited by examiner

$E_{k,1}$ → compensated for the focal energy loss by steering
→ compensate for preferential border cooling because of diffusion

FIG. 3

CONTROLLER MODIFICATION COMPARED TO INITIAL PID

| Symbols | $\Theta(t)$ : prescribed (or target) evolution of the temperature<br>$T(\vec{r}_o,t)$ : experimental (measured) temperature point $\vec{r}_o$ time $t$<br>$\Delta(\vec{r}_o,t) = \Theta(t) - T(\vec{r}_o,t)$ : current error at location $\vec{r}_o$<br>$\Omega(\vec{r}_o,t) = \int_0^t [\Theta(t') - T(\vec{r}_o,t')]dt'$ : integrated error at location $\vec{r}_o$ | |
|---|---|---|
| | PID algorithm | P2ID algorithm |
| Master equation for updating the applied power | $P(\vec{r}_o,t) = \dfrac{1}{\alpha(\vec{r}_o)} \left\{ \dfrac{d\Theta(t)}{dt} + D \cdot \nabla^2 T(\vec{r}_o,t) + q \cdot \Delta(\vec{r}_o,t) + \dfrac{q^2}{4} \cdot \Omega(\vec{r}_o,t) \right\}$ | $P(t) = \dfrac{1}{\alpha(\vec{r}_o)} \left\{ \dfrac{d\Theta(t)}{dt} + D \cdot \nabla^2 T(\vec{r}_o,t) + w \cdot t \cdot \Delta(\vec{r}_o,t) + w \cdot \Omega(\vec{r}_o,t) \right\}$ |
| Recommended values for negative reaction whilst noise-robust | $q \approx \dfrac{0.20}{sampling\_time} \ldots \dfrac{0.25}{sampling\_time}$ | $w \approx \dfrac{0.20}{(sampling\_time)^2} \ldots \dfrac{0.25}{(sampling\_time)^2}$ |
| Characteristic differential equation | $\dfrac{d^2\Omega}{dt^2} + q \cdot \dfrac{d\Omega}{dt} + \dfrac{q^2}{4} \cdot \Omega = 0$ | $\dfrac{d^2\Omega}{dt^2} + w \cdot t \cdot \dfrac{d\Omega}{dt} + w \cdot \Omega = 0$ |
| Time domain convergent solution (TDCS) | $\Omega(t) \propto \left(1 - \dfrac{q \cdot t}{2}\right) \cdot exp\left(-\dfrac{q \cdot t}{2}\right)$ | $\Omega(t) \propto exp\left(-\dfrac{w \cdot t^2}{2}\right)$ |
| Numerical simulation of convergence when confronted with varying absorption coefficient of HIFU in tissue |  |  |
| Convergence time | $\dfrac{2}{q}$ : typical 8…10 sampling points | $\sqrt{\dfrac{2}{w}}$ : typical $\sqrt{8} \ldots \sqrt{10}$ sampling points |

FIG. 4

CONTROLLER MODIFICATION TO NON-PARAMETRIC AND DISCRETE-TIME IMPLEMENTATION

| | Parametric & continuous time description | Non-parametric & discrete-time implementation with adimensional numbers |
|---|---|---|
| Controlled variable | $T(\vec{r}_o, t)$ | MR-measured temperature<br>$T_{k,n}$ : $k$ = spatial index over foci $1:N_f$<br>$n$ = MRT scan index |
| Target value | $\Theta(t)$ | $\Theta_n$ : $n=1,2,3,...$ MRT scan index |
| Definition of target | Continuous and derivable scalar function (rising portion + flattop region) | $\Theta_n = \begin{cases} \dfrac{1}{N_f}\sum\limits_{k=1}^{N_f} T_{k,n} & if \quad \Theta_n \leq \Theta_{top} - \delta \Leftrightarrow n \leq n_{switch} \\ \Theta_{top} & if \quad \Theta_n > \Theta_{top} - \delta \Leftrightarrow n > n_{switch} \end{cases}$ |
| Graphical view of target curve/ target domain | Temperat. Elevation [0]<br><br>Rising curve from 0 reaching 20 at ~75 sec, flat at 20 until ~150 sec, then drops to 0<br>Time [sec] 0–200 | Temperat. Elevation [ ]<br><br>Scattered points approaching $\Theta_{top}$ (with $\delta$ band), then decaying<br>Regim transitio ris \| stead-stat, $n_{switch}$<br>Time [sec] 0–200 |
| Current error | $\Delta(\vec{r}_o, t) = \Theta(t) - T(\vec{r}_o, t)$ | $\Delta_{k,n} = 1 - \dfrac{T_{k,n}}{\Theta_n}$ : relative error (focus $k$, scan $n$) |
| Integral error | $\Omega(\vec{r}_o, t) = \int\limits_0^t [\Theta(t') - T(\vec{r}_o, t')]dt'$ | $\Omega_{k,n} = \sum\limits_{n'=1}^{n}\left(1 - \dfrac{T_{k,n'}}{\Theta_{n'}}\right)$ : cumulative relative error |
| Controller output | $P(\vec{r}_o, t) = \dfrac{1}{\alpha(\vec{r}_o)} \left\{ \begin{array}{l} \dfrac{d\Theta(t)}{dt} + D \cdot \nabla^2 T(\vec{r}_o, t) + \\ + w \cdot t \cdot \Delta(\vec{r}_o, t) + w \cdot \Omega(\vec{r}_o, t) \end{array} \right\}$ | $w^* = w \cdot \tau^2$ with $\tau$ = temporal resolution<br>$P_{k,n} = P_{k,1} \cdot (1 + F_{k,n})$ with $n \geq 2$ : power modulation<br>$E_{k,n} = E_{k,1} \cdot (1 + F_{k,n})$ with $n \geq 2$ : energy modulation<br>$F_{k,n+1} = \begin{cases} w^* \cdot n \cdot \left(1 - \dfrac{T_{k,n}}{\Theta_n}\right) + w^* \cdot \Omega_{k,n} & if \; n \leq n_{switch} \\ -1 + \tanh(0.025 * n_{switch}) + w^* \cdot n \cdot \left(1 - \dfrac{T_{k,n}}{\Theta_{top}}\right) + w^* \cdot \Omega_{k,n} & else \end{cases}$ |

METHOD FOR TEMPERATURE CONTROL IN MAGNETIC RESONANCE-GUIDED VOLUMETRIC ULTRASOUND THERAPY

BACKGROUND OF THE INVENTION

1. Field of the Invention

The present invention concerns a method for controlling temperature in a patient undergoing ultrasound therapy under the guidance of magnetic resonance thermometry, and in particular to a rapidly convergent, multi-input, multi-output, non-parametric temperature controller for implementing such a method.

2. Description of the Prior Art

The localized application of ultrasound to treat certain types of local cancer often takes place with the patient being located, during the therapy, in a magnetic resonance imaging system, so that the temperature of the patient can be monitored by magnetic resonance thermometry. Magnetic resonance thermometry is a known manner of monitoring the temperature of an examination subject while the subject is located in a magnetic resonance data acquisition unit (scanner), and is based on the known phenomenon that the magnetic resonance signals emitted by nuclear spins in the examination subject, which have been forced out of a steady-state condition by the application of energy thereto, are temperature-dependent. The precessing nuclear spins that have been forced out of their equilibrium state emit signals that are detected and are used for conventional magnetic resonance imaging. The temperature-dependency of these signals also allows a temperature map of the examination subject to be generated, that very precisely shows temperature variations along multiple axes.

High intensity ultrasound is effective for use in treating localized cancers or other pathologies. For this purpose, the high intensity focused ultrasound (HIFU) is administered.

In order to steer and focus the therapeutic ultrasound, such an ultrasound head or device typically has multiple ultrasound emitters (transducers) arranged and operated in an array.

In general terms, magnetic resonance guiding or monitoring of such therapy takes place by administering HIFU to the patient in the examination region of a magnetic resonance scanner. Magnetic resonance data are acquired in a known manner from the patient in the scanner while the ultrasound therapy is in progress. In real-time with the therapy, magnetic resonance thermometry images of the patient are generated, showing the temperature distribution within a designated region of the patient. The resulting MR thermometry image can be shown on a monitor in real-time during the therapy for visual review and manual control of the therapy by a physician or a technician, or known image processing techniques can be used in order to generate appropriate extractions of information from the thermometry image for use in automatic control of the therapy.

An overview of MR-guided focused ultrasound hyperthermia is described in "Hyperthermia by MR-guided Focused Ultrasound: Accurate Temperature Control Based on Fast MRI and A Physical Model of Local Energy Deposition and Heat Conduction," Salomir et al., Magnetic Resonance in Medicine, Vol. 43 (2000) pages 342-347. Various automatic control techniques are described, for example, in "Automatic Spatial and Temporal Temperature Control for MR-Guided Focused Ultrasound Using Fast 3D MR Thermometry and Multispiral Trajectory of the Focal Point," Mougenot et al., Magnetic Resonance in Medicine, Vol. 52 (2004) pgs 1005-1015; "Three-Dimensional Spatial and Temporal Temperature Control with MR Thermometry-Guided Focused Ultrasound (MRgHIFU)," Mougenot et al., Magnetic Resonance in Medicine, Vol. 61 (2009) pgs 603-614 and "Curvilinear Transurethral Ultrasound Applicator for Selective Prostrate Thermal Therapy," Ross et al., Medical Physics, Vol. 32, No. 6 (2005) pgs 1555-1565. A prevalent technique for temperature control in such therapy is to make use of a proportional-integral-derivative (PID) controller. In general terms, PID controller calculates an error value as the difference between a measured process variable and a desired reference point. As indicated by its name, a PID controller makes use of three feedback reaction terms, respectively referred to as proportional, integral and derivative values. The proportional value is dependent on the current error, the integral value represents an accumulation of past error, and the derivative value represents a prediction of future errors, based on a current rate of change. Typically, a weighted sum of these three values is used to adjust the process in question, by adjusting some type of control element that has the capability of changing the monitored parameter of the process in question. A study of the use of PID temperature control in the context of MRI-guided phased-array contact ultrasound is provided in "Endocavitary Thermal Therapy by MRI-guided Phased-Array Contact Ultrasound: Experimental and Numerical Studies on the Multi-input Single-Output PID Temperature Controller's Convergence and Stability," Salomir et al., Medical Physics, Vol. 36, No. 10 (2009) pgs 4726-4741.

The PID-based controller in general exhibit good stability and robustness to noise, but its convergence is rather slow. When the number of temperature sampling points during the controlled sonication is low, the PID algorithm does not have sufficient time to adjust the power level so as to compensate for local variability in heat deposition or tissue cooling by diffusion/perfusion. The condition is worsened when the total time base is short, at the scale of the tissue response time to an elementary heat source. Moreover, when the static tuning of the physical parameters in the underlying model is far from the true parameters, overshooting of the temperature curves occurs with transient but significant and possibly longer heating above the prescribed temperature.

SUMMARY OF THE INVENTION

It is an object of the present invention to provide an improved temperature control algorithm for use in MRI-guided phased-array contact ultrasound that is particularly suited for cycled sonication along a volumetric pattern that is repeated for each MR dynamic scan.

It is a further object of the present invention to provide such a temperature control algorithm that delivers an equivalent thermal dose in every focus in a time interval of 20 to 30 times the duration of the MR-thermometry measurement.

The above object is achieved in accordance with the present invention by a method for temperature control in MR-guided administration of ultrasound wherein the temperature in a localized region of an examination subject is monitored in real-time by MR thermometry and, from the MR thermometry, characteristics of the temperature distribution in the monitored region of the examination subject are automatically identified and are employed in a computerized processor to implement temperature control, by regulating the ultrasound therapy device.

The temperature controller is designed in two steps: 1) the classic PID equation is modified for improved convergence, and 2) the algorithm is rendered non-parametric by considering the relative offset of temperature of a given focus with respect to the average temperature calculated over all the foci.

The classic equation of a PID controller is modified into:

$$P(t) = \frac{1}{\mu(\vec{r}_o)} \left\{ \frac{d\Theta(t)}{dt} + D(\vec{r}_o) \cdot \nabla^2 T(\vec{r}_o, t) + w \cdot t \cdot \Delta(\vec{r}_o, t) + w \cdot \Omega(\vec{r}_o, t) \right\}$$

wherein $\mu(\vec{r}_o)$ is the ultrasound absorption point $\vec{r}_o$ $D(\vec{r}_o)$ is the heat diffusivity point $\vec{r}_o$ $\Theta(t)$ is the prescribed (or target) evolution of the temperature, $T(\vec{r}_o, t)$ is the experimental (measured) temperature point $\vec{r}_o$ time t, $\Delta(\vec{r}_o, t) = \Theta(t) - T(\vec{r}_o, t)$ is the current error at location $\vec{r}_o$; and $$\Omega(\vec{r}_o, t) = \int_0^t [\Theta(t') - T(\vec{r}_o, t')] dt'$$

is the integrated error at location $\vec{r}_o$.

The characteristic differential equation in accordance with the invention is:

$$\frac{d^2\Omega}{dt^2} + w \cdot t \cdot \frac{d\Omega}{dt} + w \cdot \Omega = 0$$

The time domain convergence solution is:

$$\Omega(t) \propto \exp\left(-\frac{w \cdot t^2}{2}\right)$$

The convergence time is $(2/w)^{1/2}$, typically for value being $\sqrt{8}$ to $\sqrt{10}$ sampling points. A value for the negative reaction w can be selected in a range between 0.01 divided by the square of the sampling time, and 10.0 divided by the square of the sampling time. Recommended values for the negative reaction (denoted w) are in a range between 0.20 divided by the square of the sampling time, and 0.25 divided by the square of the sampling time.

In accordance with the present invention, a feedback control algorithm is employed wherein the negative reaction from the actual error (e.g., deviation or offset) of the measured temperature relative to a target is increased linearly with time. The temperature controller in accordance with the invention is based on a second order differential equation that is linear but with non-constant coefficients, wherein the solution is in the form of $\exp(-w \cdot t^2/2)$, wherein t=time and w is a constant. Such a solution is more stable and rapidly converging than the solution of the PID equation, of the form $(1+a \cdot t) \cdot \exp(-q \cdot t/2)$, wherein a and q are different constants.

The reference value of temperature, that is used to compare if the local temperature at a given focus has a positive or negative offset at a given time point, is defined by the following expression (instead of a continuous predefined target curve as it used to be the case for previous PID-based reports):

$$\Theta_n = \begin{cases} \frac{1}{N_f} \sum_{k=1}^{N_f} T_{k,n} & \text{before the steady state regimen} \\ \Theta_{top} & \text{during the steady state regimen} \end{cases}$$

Note that $\Theta_n$ is the spatial average of temperature values $T_{k,n}$ over the $N_f$ heated points (i.e. the sonicated foci) before the steady-state regimen was established and that $\Theta_n$ becomes identical to the prescribed target temperature after the steady-state regimen has been reached ($\Theta_{top}$, i.e. the flattop segment of the target curve). The temperature control algorithm disclosed herein aims to minimize or to null the relative offsets $$\Delta_{k,n} = 1 - \frac{T_{k,n}}{\Theta_n}.$$

The offset and the integral of the offset are calculated in each control point and these calculi are used to modulate the amount of energy delivered to each focus. The method in accordance with the present invention thereby homogenizes the temperature history of all heated locations.

The convergence of the controller is considered powerful enough to perform accurately even without a priori knowledge on heated tissue parameters. Therefore any tissue dependent parameters are discarded from the controller's equation. This condition simplifies the practical procedure of treatment and avoids the need for identification of parameters (subject to errors, time-consuming etc). The controller is therefore non-parametric, because no a priori hypothesis is made on the ultrasound absorption, the beam propagation (other than the fact that a focus must exist), heat diffusion, perfusion rate, etc. In other words, the master equation that is used to adjust the energy to be delivered at a given location uses no a priori parameter.

The feedback compensation of delivered energy at each focus is updated for each new dynamic scan, based on either the relative offset in temperature at that location as compared to the average temperature overall foci, during the rising portion of the heating curve, or the relative offset in temperature at that location as compared to the prescribed target value, during the steady state portion of the heating curve.

The method in accordance with the invention achieves faster convergence for a spatially homogenous temperature considered over all of the control points, namely approximately 10-15 temporal sampling points. The method according to the invention achieves higher accuracy, which means a reduced amplitude of any overshooting or undershooting of the experimental temperature curve, even when confronted by significant changes in the energy deposition from one heating location to another, or when confronted with dynamic changes of tissue properties.

DESCRIPTION OF THE PREFERRED EMBODIMENTS

Figure 13:
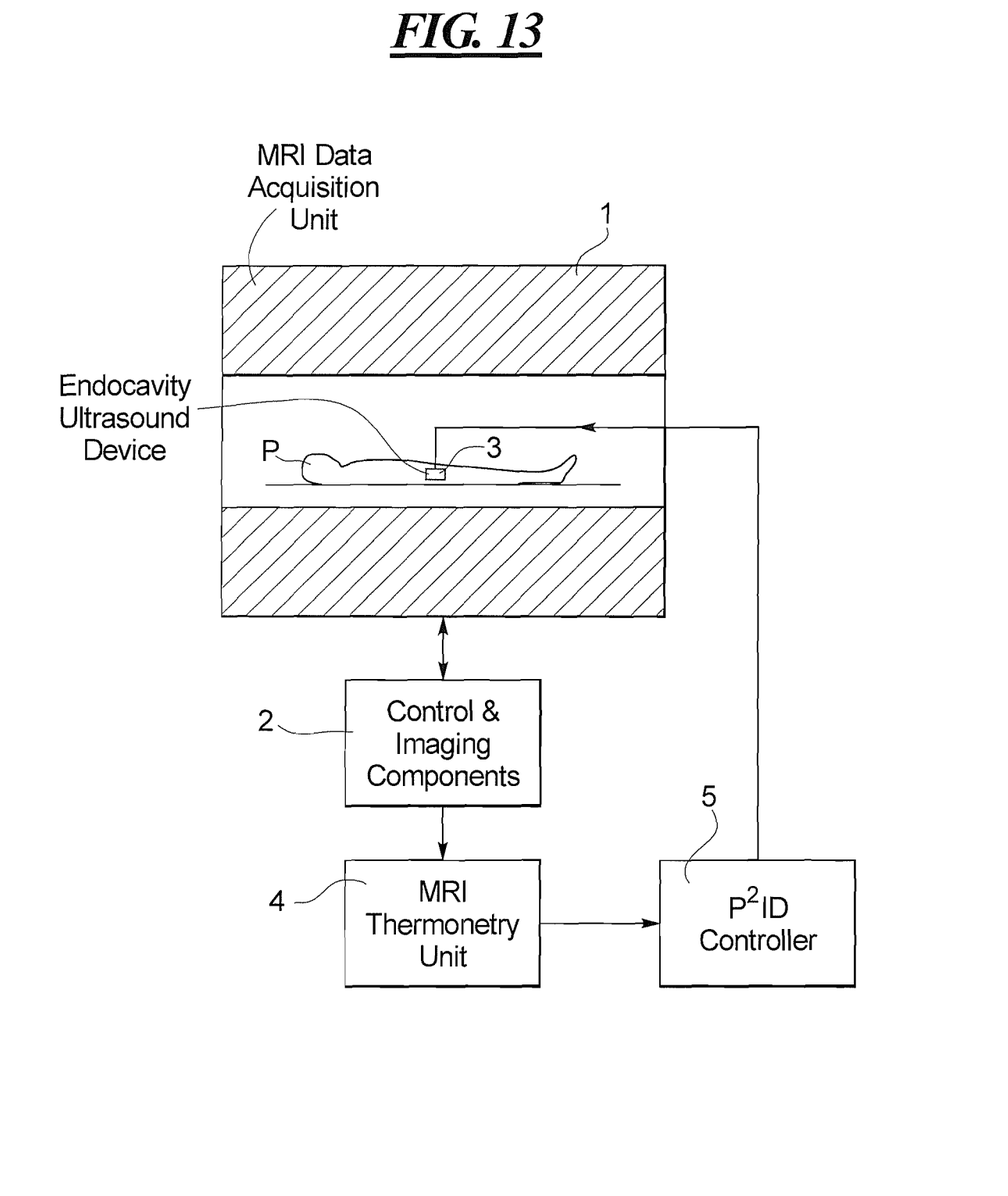
FIG. 13 schematically illustrates the basic components for implementing the method in accordance with the present invention.

FIG. 13 schematically illustrates the basic components of MR-guided ultrasound therapy, such as high intensity focused ultrasound (HIFU). For this purpose, a patient P is placed in a magnetic resonance imaging data acquisition unit 1, which is operated in a known manner by control and imaging components 2. A high intensity focused ultrasound device, such as a multi-focus device, and is operated to implement sonication of the patient P at a localized site at which, for example, cancer tissue had been determined to be located. The MR data acquired from the patient P in a localized region in which the ultrasound has been administered are processed in a known manner in an MR thermometry unit 4, in order to obtain an electronic representation of the temperature distribution in the localized region of the patient P produced by operation of the ultrasound device 3. An image representing this temperature distribution can be displayed at a monitor (not shown) for visual examination and use by a technician or a physician. Additionally, relevant information can be electronically obtained or extracted from the thermometry representation, and supplied to pay controller 5 that operates the ultrasound device 3 by controlling ultrasound emission from the respective foci thereof. The controller 5, in accordance with the invention, is designated as a $P^2ID$ controller, in order to distinguish it from the conventional PID controller that is commonly used.

The volumetric sonication that is implemented in accordance with the present invention is accomplished by rapidly iterated (activated) foci, the activation taking place at the time scale of heat diffusion in the tissue being insonified. The thermal build-up (distribution) is constructed as a spatially continuous function, such as by repeated cycles of sonication along the same sonication pattern, with one cycle duration being equal to the cycle of one MR dynamic scan (i.e., data acquisition or measurement cycle). The number of foci forming the pattern is $N_f \geq 2$, and they are sonicated nearly simultaneously using a phased-array electronic steering of the beam. The distance between foci (inter-focus spatial gap) must be larger than the intrinsic size of the focal spot for individual identification, but should not be so large as to permit the formation of a continuous thermal build-up by exploiting heat diffusion.

Figure 1:
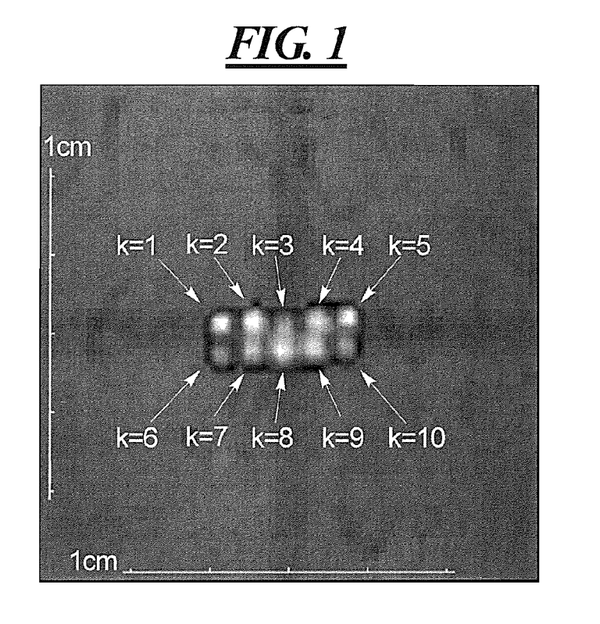
FIG. 1 is an image of a multi-focus pattern for volumetric sonication of a subject of the type that is controlled in accordance with the present invention.
Figure 2:
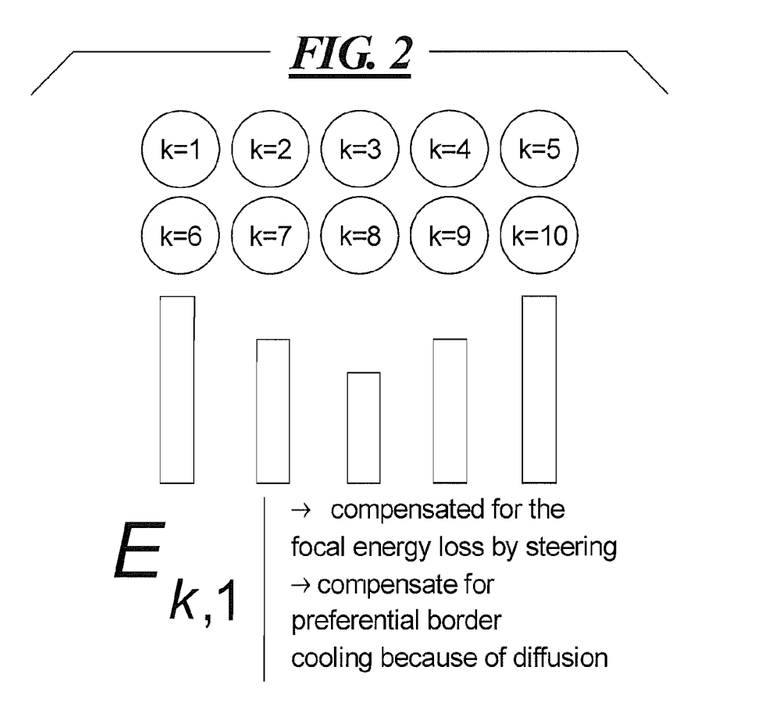
FIG. 2 schematically illustrates the initial amount of energy $E_k, 1$ prescribed for each focus.
Figure 3:
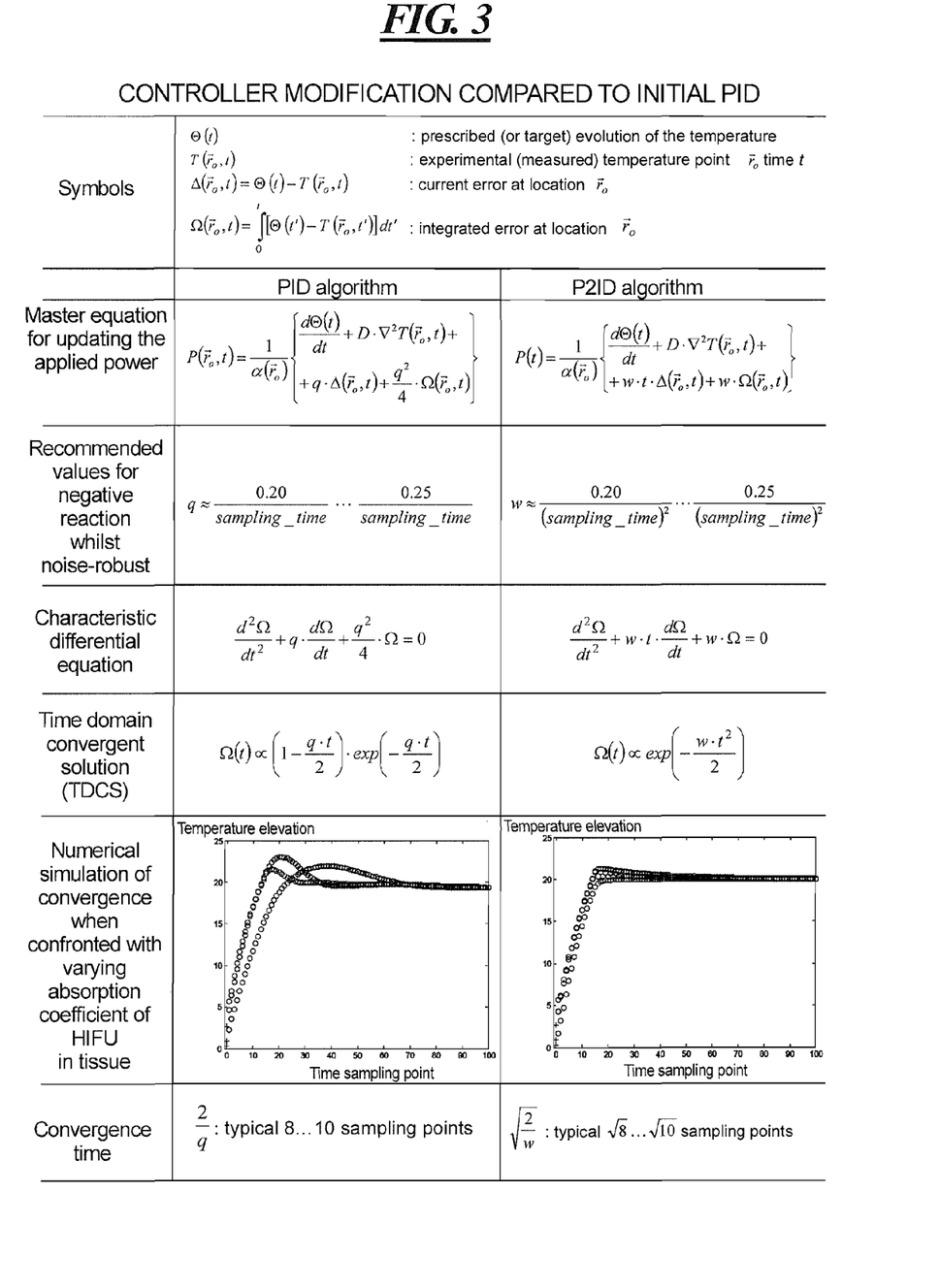
FIG. 3 is a comparison of the controller modification in accordance with the present invention compared to conventional PID control.
Figure 4:
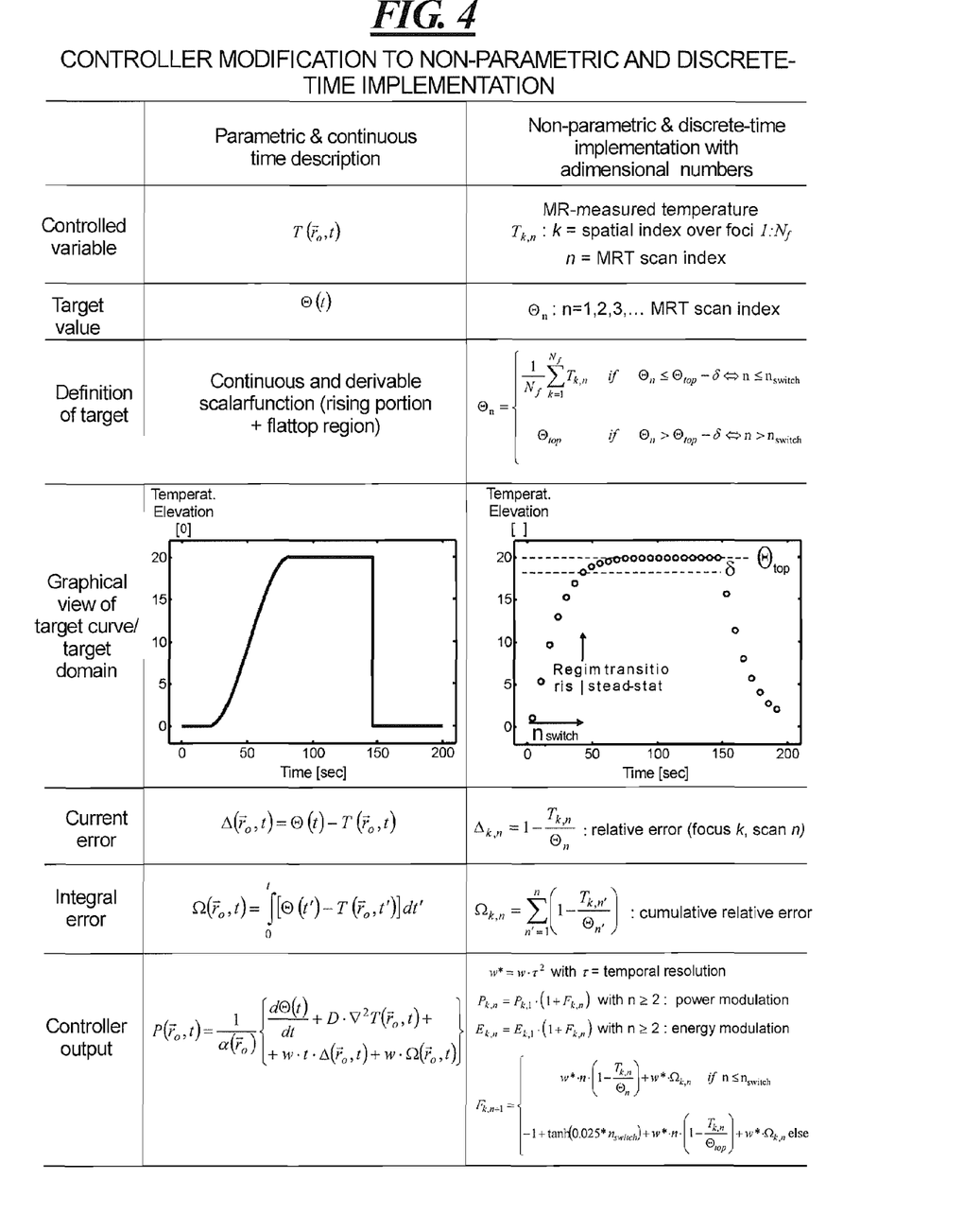
FIG. 4 is a comparison of the controller modification in accordance with the present invention compared to parametric and continuous time control.

FIG. 1 illustrates a multi-focus pattern for volumetric pattern having ten individual foci $N_f=10$ as an example. Index k references the foci $1:N_f$ and $E_{k,1}$ is the initial amount of energy prescribed to each focus (scan=1), compensated for (a-priori) the energy loss by steering and for the preferential heat diffusion at borders. During the procedure, $E_{k,1}$ will be dynamically modulated by the temperature controller at each scan number n to become $E_{k,n}=E_{k,1}+\delta E_k(n)$, to insure similar temperature elevation at each foci, as schematically illustrated in FIG. 2.

The principles of treatment are as follows:

1. a sonication-cycle represents the sequential displacement of the focus through all prescribed foci; the coordinates of the prescribed foci are fixed through the full duration of the treatment;

The abstract has been amended as follows:

In a method for temperature control in MR-guided administration of ultrasound, ultrasound therapy is administered to a patient at an in vivo site by emitting focused ultrasound into the site at multiple foci with a multi-focus ultrasound therapy device. The temperature is monitored in a localized region of an examination subject in which the site is located during the therapy in real-time by MR thermometry. From the MR thermometry, characteristics of the temperature distribution in the monitored region of the examination subject are automatically identified. Temperature control is implemented by regulating the energy output of the ultrasound therapy device, according to a rapidly converging master equation.

$$\frac{\delta E_k(n)}{E_{k,1}} = \begin{cases} w^* \cdot n \cdot \left(1 - \frac{T_{k,n}}{\Theta_n}\right) + w^* \cdot \Omega_{k,n} & \text{if } n \leq n_{switch} \\ -1 + \tanh(\alpha \cdot n_{switch}) + w^* \cdot n \cdot \\ \quad \left(1 - \frac{T_{k,n}}{\Theta_{top}}\right) + w^* \cdot \Omega_{k,n} & \text{else} \end{cases}$$

wherein tanh is the analytical function hyperbolic tangent, $n_{switch}$ denotes the sampling point where the controller switches irreversibly from the rapid temperature elevation regimen to the steady state regimen, $\alpha$ is a positive number in general smaller than 0.1 (recommended to be approximately 0.025), $T_{k,n}$ is the actual temperature at the sonicated focus k for the measurement n, $\Theta_n$ is the average value of measured temperatures $T_{k,n}$ over the sonicated foci for measurement n, $\Theta_{top}$ is the flattop target value of steady state temperature elevation, $w^*$ is the negative feedback parameter a-dimensional and scaled to the square of the temporal resolution ($\tau$) as $w^*=w/\tau^2$, and $\Omega_{k,n}$ is the cumulative relative offset (or, error) of the measured temperature until the measurement n:

$$\Omega_{k,n} = \begin{cases} \sum_{n'=1}^{n} \left(1 - \frac{T_{k,n'}}{\Theta_{n'}}\right) & \text{if } n \leq n_{switch} \\ \sum_{n'=1}^{n_{switch}} \left(1 - \frac{T_{k,n'}}{\Theta_{n'}}\right) + \sum_{n'=n_{switch}+1}^{n} \left(1 - \frac{T_{k,n'}}{\Theta_{top}}\right) & \text{if } n > n_{switch} \end{cases}$$

During the steady state regime (starting at the sampling point $n_{switch}+1$), the term $\tan h(\alpha \cdot n_{switch})$ takes into account the predicted amount of energy (relative to the initial value at n=1) necessary to maintain the steady state (constant temperature) in homogeneous tissue; inhomogeneities are managed for by the feedback terms proportional and integral. Based on the behavior of the hyperbolic-tangent function: a). if the tissue reaches rapidly the target top temperature, this means the maintaining energy is low; b). when $n_{switch}$ increases to infinity, the full energy is necessary to maintain the steady state.

The controller algorithm decides when to switch to the state-state computing equation, meaning when the sampling point is declared equal to $n_{switch}$.

This is done in a predictive manner.

Sampling point "n" becomes "$n_{switch}$" if following condition is fulfilled:

$$[\theta_n + (\theta_n - \theta_{n-1})] > (\theta_{top} - \delta) \text{ or } \theta_{top} - 2\cdot\theta_n + \theta_{n-1} < \delta$$

Textually, this means that the predicted temperature elevation after one more sonication cycle will exceed the transition level. Here $\delta = 0.5°$ C. The predicted temperature elevation is the actual value plus the last increment between the previous and actual cycle.

The transition is decided irreversibly. Once the master equation was switched to the steady-state form, this one will be used until the end of the active heating.

According to equations provided above, the proportional term brings a negative reaction that linearly increases with time. Because the temperature data are contaminated by experimental noise, over weighted negative reaction can drive the controller into instability.

Moreover, it is important that the negative reaction increases linearly during the "learning" stage, which corresponds to the time interval of the first 10 to 15 dynamics.

Once the temperature reached the steady-state level ("cruise altitude"), the heating device only needs to compensate for local cooling by diffusion and perfusion, and the negative reaction can be stabilized.

Therefore we modify the master equation for the controller output, by limiting the negative reaction of the proportional term ($n \leq n_{max}$) as follows:

A. Threshold limitation of the negative reaction of proportional term $$\frac{\delta E_k(n)}{E_{k,1}} = \begin{cases} w^* \cdot \min(n, n_{max}) \cdot \left(1 - \frac{T_{k,n}}{\Theta_n}\right) + w^* \cdot \Omega_{k,n} & \text{if } n \leq n_{switch} \\ -1 + \tanh(\alpha^* n_{switch}) + w^* \cdot \min(n, n_{max}) \cdot \\ \left(1 - \frac{T_{k,n}}{\Theta_{top}}\right) + w^* \cdot \Omega_{k,n} & \text{else} \end{cases}$$

Figure 5:
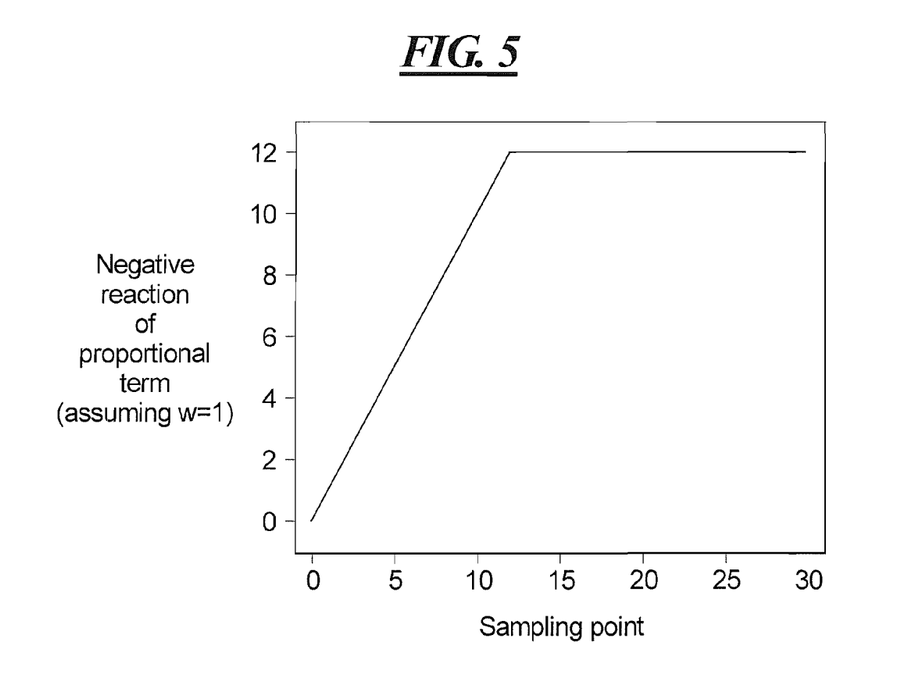
FIG. 5 is a graph illustrating the threshold limitation of the negative reaction of the proportional term.

The plot for a recommended value $n_{max} = 12$ is shown in FIG. 5.

B. Hyperbolic tangent limitation of the negative reaction of the proportional term $$\frac{\delta E_k(n)}{E_{k,1}} = \begin{cases} w^* \cdot n_{max} \cdot \tanh\left(\frac{n}{n_{max}}\right) \cdot \left(1 - \frac{T_{k,n}}{\Theta_n}\right) + w^* \cdot \Omega_{k,n} & \text{if } n \leq n_{switch} \\ -1 + \tanh(\alpha^* n_{switch}) + w^* \cdot n_{max} \cdot \tanh\left(\frac{n}{n_{max}}\right) \cdot \\ \left(1 - \frac{T_{k,n}}{\Theta_{top}}\right) + w^* \cdot \Omega_{k,n} & \text{else} \end{cases}$$

Figure 6:
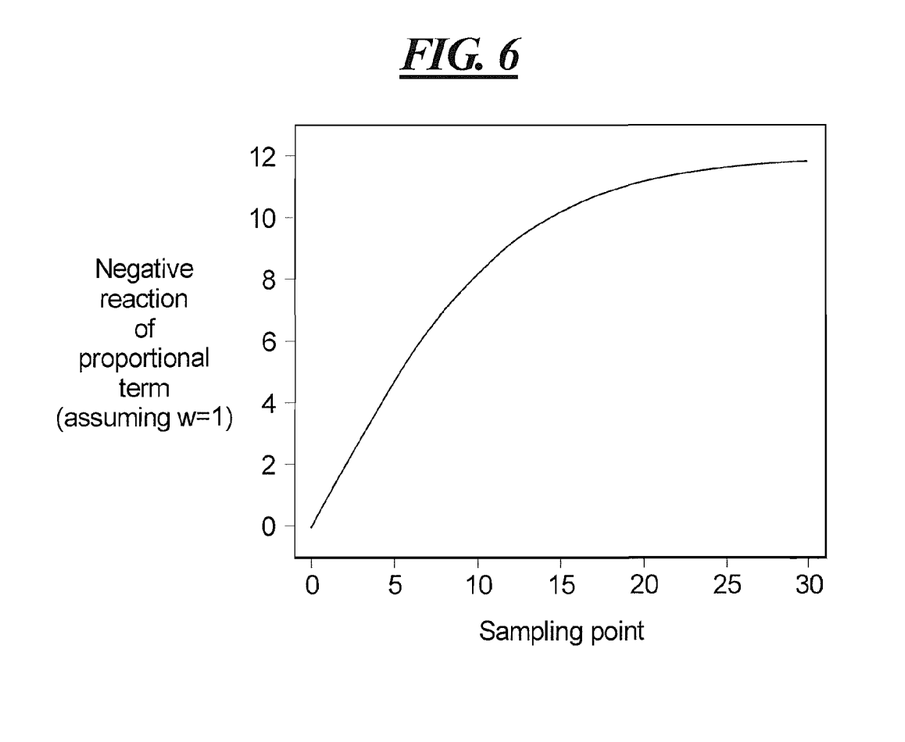
FIG. 6 is a graph illustrating the hyperbolic tangent limitation of the negative reaction of the proportional term.

The plot for a recommended value $n_{max} = 12$ is shown in FIG. 6.

Figure 7:
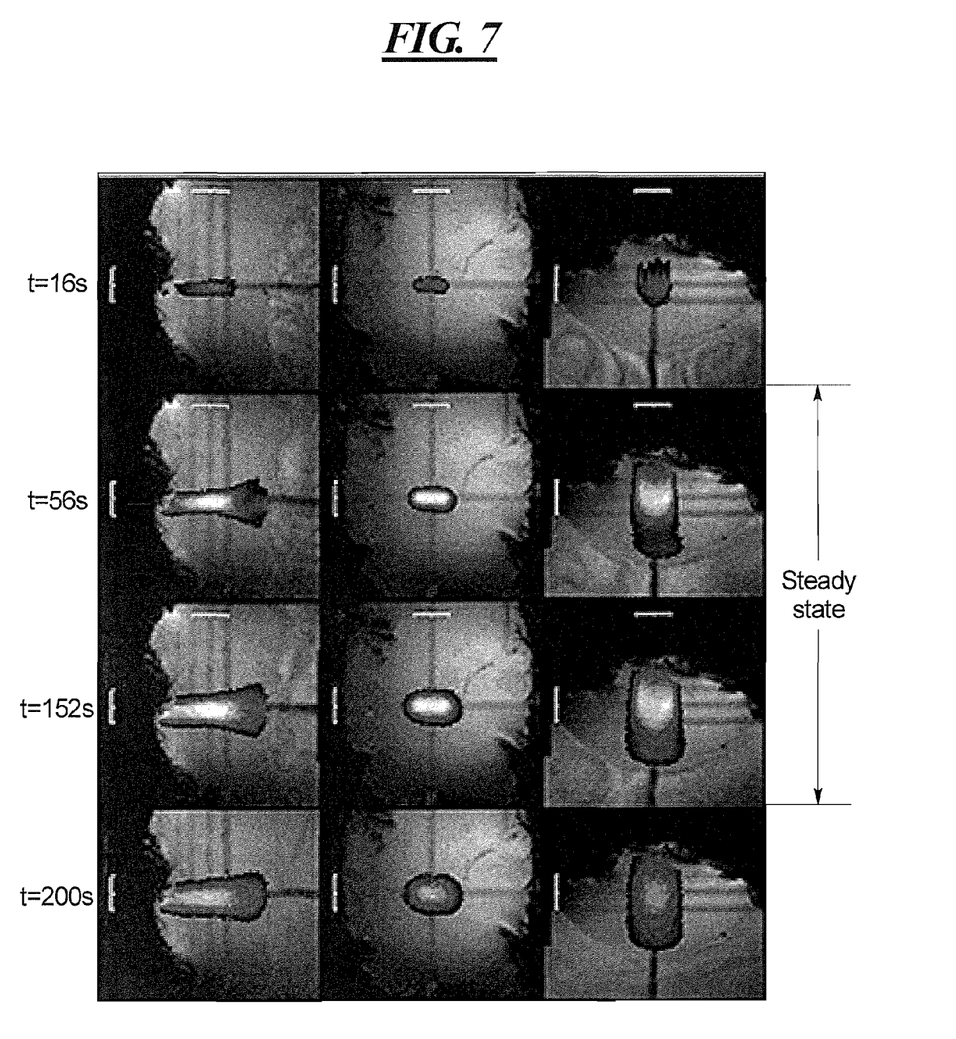
FIG. 7 illustrates temperature maps on magnitude images for three orthogonal planes during magnetic resonance guided high intensity focused ultrasound (HIFU) sonication, with control in accordance with the present invention.

FIG. 7 shows temperature maps overlaid on magnitude images for three orthogonal planes, during MRgHIFU sonication under active control (using the disclosed controller). The time point for each map is indicated on left. During steady state regime, the maximum (central) temperature is constant (±noise) but the edges of the thermal build up are expanding and smoothing because of diffusion (hence the interest to treat as fast as possible, provided a rapidly convergent controller).

Figure 8:
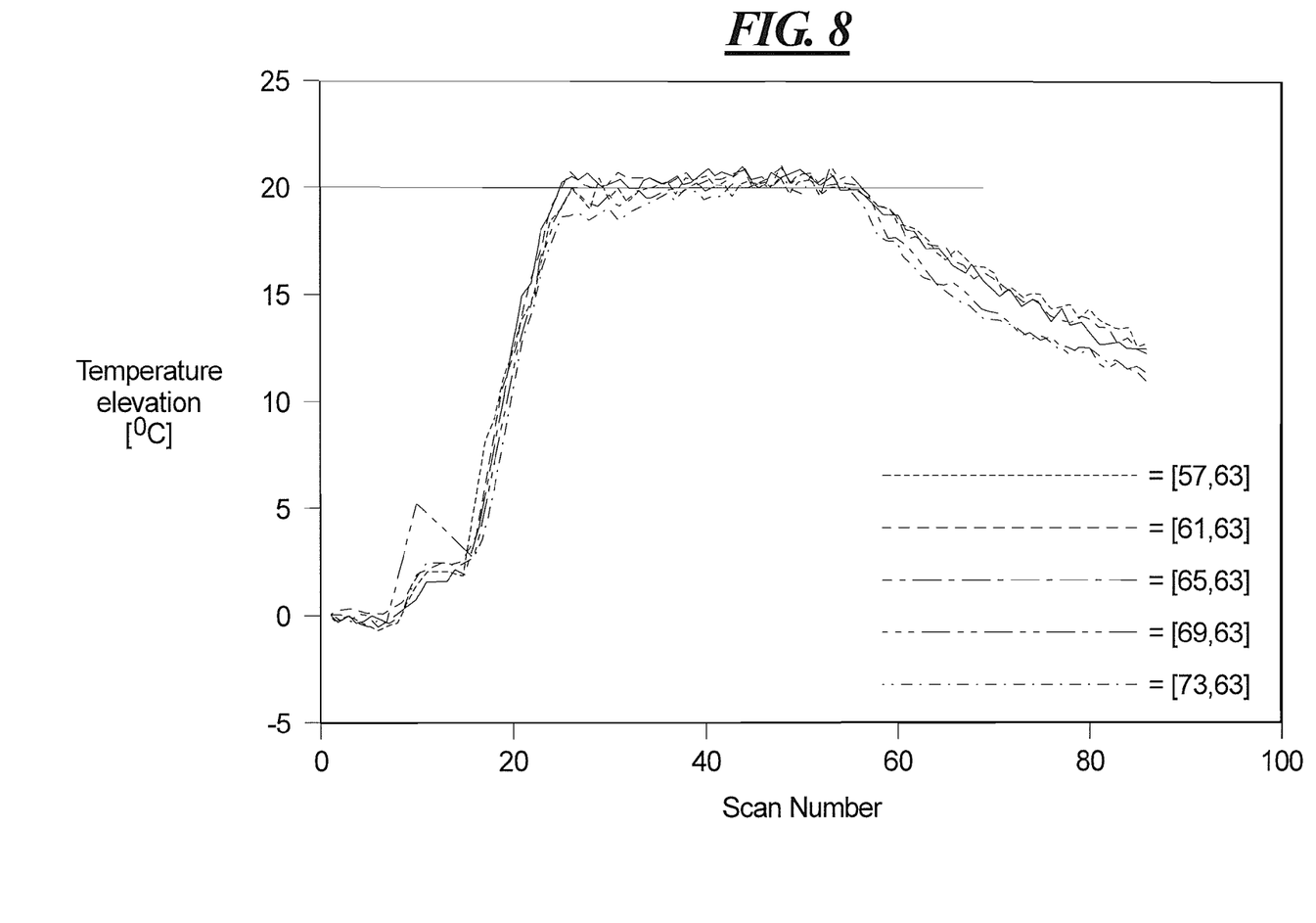
FIG. 8 illustrates the temperature evolution at 5 individual locations indicated by pixel coordinates, with temperature control in accordance with the present invention.
Figures 9A, 9B:
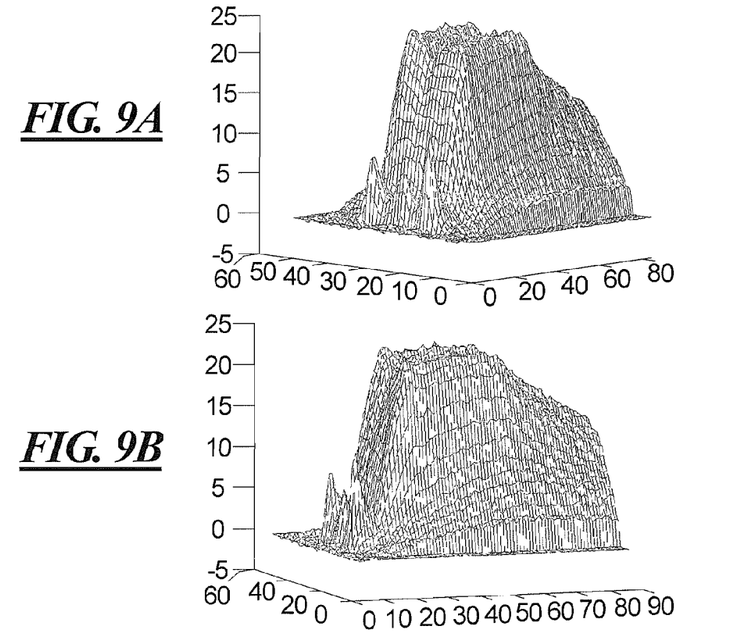
FIGS. 9A, 9B, 9C and 9D are surface representations of a 1 D temperature profile scrolled over time, for the patient for which the temperature maps of FIG. 7 were generated.
Figure 9C:
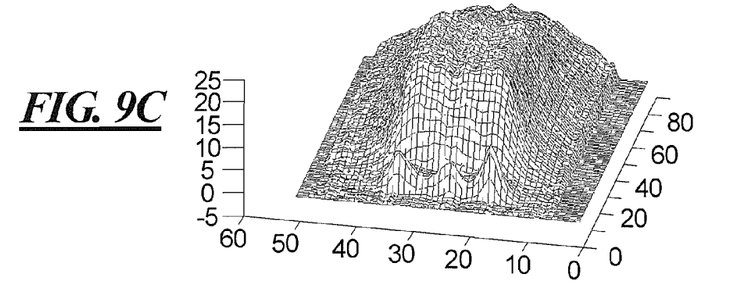
Figure 9D:
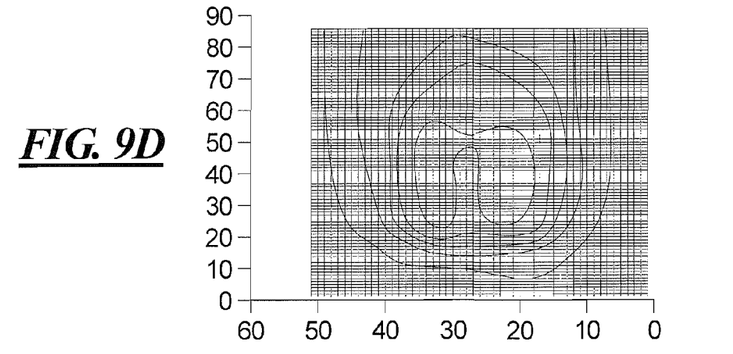

FIG. 8 shows the temperature evolution at five individual locations (pixel coordinates indicated lower right for the same experiment as FIG. 7. The similar temperature history of each focus, and the rising-temperature regime and further the steady-state regime can be seen. Foci from the pattern edge are cooling faster than central ones after sonication ended.

Figure 10:
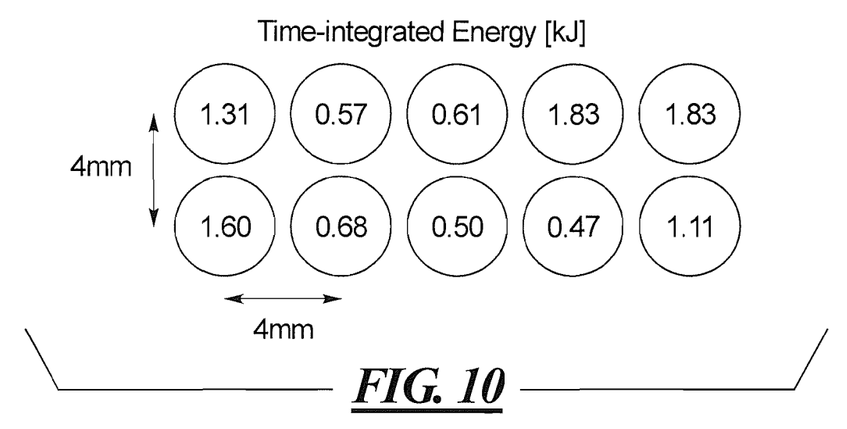
FIG. 10 schematically illustrates acoustic energy delivered per target focus in accordance with the present invention.

FIGS. 9A, 9B, 9C and 9D are surface representations of a 1D temperature profile scrolled over time, for the same experiment as for FIGS. 7 and 8. FIG. 10 shows acoustic energies delivered per target focus, as recorded by the SW interface. The edge foci received significantly more energy while undergoing similar temperature regime as central foci. This justifies the need for feedback control.

TABLE

Listing of average temperature elevation of the 10 sonicated foci over time during the actively controlled heating in one typical experiment. The inter-foci standard deviation (at a given time-point) is indicated, i.e. the degree of spatial homogeneity, and the spatially-integrated acoustic energy for each cycle. The prescribed (or, target) temperature elevation was 20° C. above the initial baseline.

| Scan/ or cycle | Average temperature [° C.] | STD over foci [° C.] | Total energy per scan equivalent, per sonication cycle [J] |
|---|---|---|---|
| 1 | 2.92 | 0.80 | 465 |
| 2 | 3.66 | 0.81 | 465 |
| 3 | 5.78 | 1.21 | 508 |
| 4 | 8.08 | 1.12 | 524 |
| 5 | 10.22 | 0.88 | 523 |
| 6 | 11.97 | 0.71 | 514 |
| 7 | 13.91 | 0.62 | 504 |
| 8 | 15.09 | 0.58 | 502 |
| 9 | 16.88 | 0.65 | 491 |
| 10 | 18.20 | 0.68 | 337 |
| 11 | 19.18 | 0.70 | 192 |
| 12 | 19.92 | 0.61 | 154 |
| 13 | 19.76 | 0.58 | 166 |
| 14 | 19.45 | 0.67 | 192 |
| 15 | 19.56 | 0.78 | 189 |
| 16 | 19.66 | 0.48 | 180 |
| 17 | 19.80 | 0.83 | 176 |
| 18 | 19.70 | 0.57 | 181 |
| 19 | 19.82 | 0.45 | 173 |
| 20 | 20.03 | 0.50 | 159 |
| 21 | 19.99 | 0.48 | 162 |
| 22 | 20.02 | 0.41 | 160 |
| 23 | 20.04 | 0.48 | 158 |
| 24 | 20.14 | 0.33 | 151 |
| 25 | 20.09 | 0.35 | 153 |
| 26 | 20.19 | 0.51 | 147 |
| 27 | 20.24 | 0.30 | 141 |
| 28 | 20.18 | 0.37 | 144 |
| 29 | 20.41 | 0.38 | 126 |
| 30 | 20.57 | 0.31 | 112 |
| 31 | 20.16 | 0.17 | 139 |
| 32 | 20.33 | 0.23 | 126 |
| 33 | 20.19 | 0.34 | 136 |
| 34 | 20.59 | 0.36 | 105 |

TABLE-continued

Listing of average temperature elevation of the 10 sonicated foci over time during the actively controlled heating in one typical experiment. The inter-foci standard deviation (at a given time-point) is indicated, i.e. the degree of spatial homogeneity, and the spatially-integrated acoustic energy for each cycle. The prescribed (or, target) temperature elevation was 20° C. above the initial baseline.

| Scan/ or cycle | Average temperature [° C.] | STD over foci [° C.] | Total energy per scan equivalent, per sonication cycle [J] |
|---|---|---|---|
| 35 | 20.16 | 0.32 | 133 |
| 36 | 20.39 | 0.35 | 116 |
| 37 | 20.40 | 0.16 | 113 |
| 38 | 20.05 | 0.25 | 137 |
| 39 | 20.56 | 0.32 | 101 |
| 40 | 20.16 | 0.21 | 125 |

Figure 11:
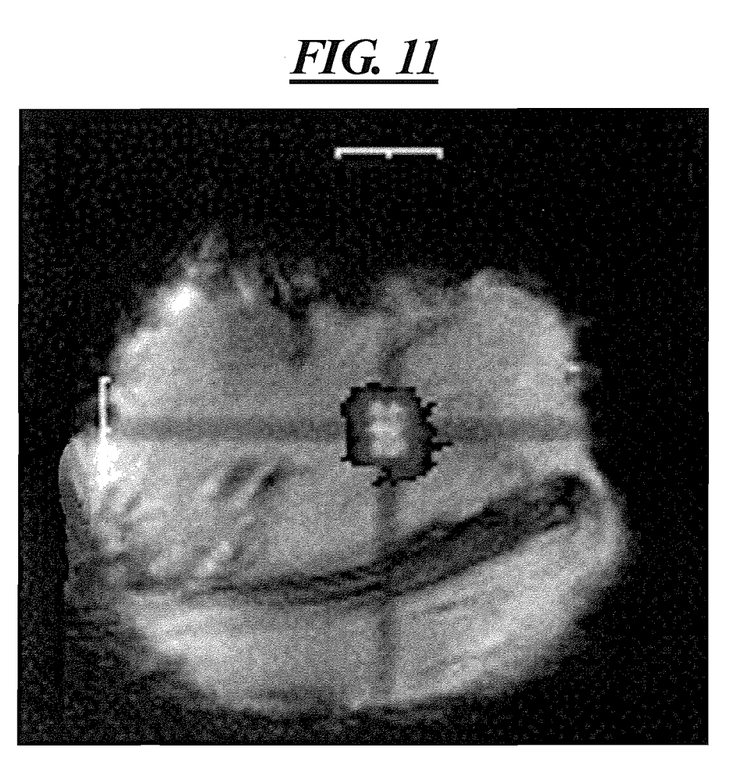
FIG. 11 is a temperature map overlaid on a magnitude image in the coronal plane during six-focus sonication in a rabbit thigh, in accordance with the present invention.
Figure 12:
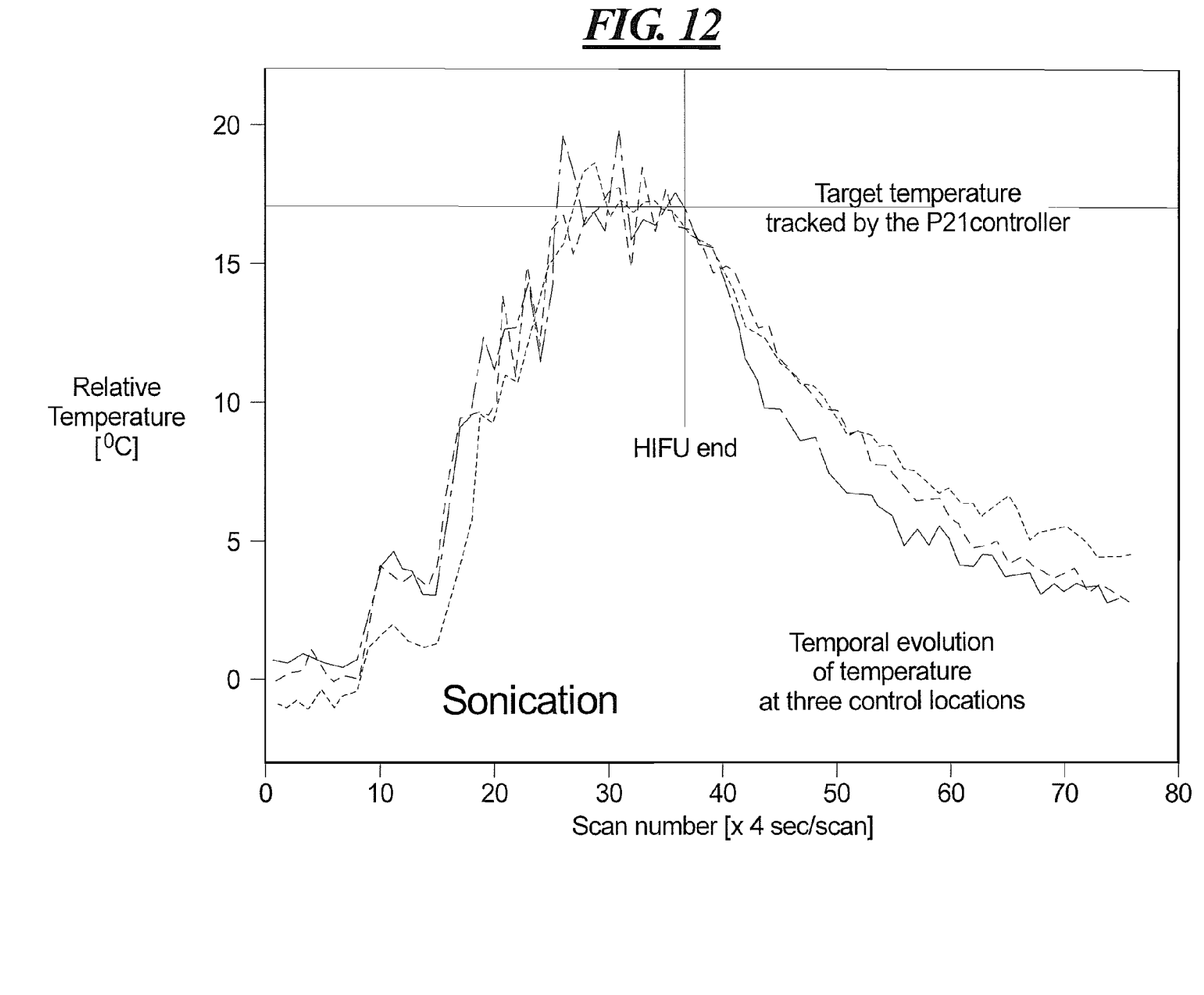
FIG. 12 shows the temperature evolution in three of the six foci in the sonication of the rabbit thigh shown in FIG. 11.

FIG. 11 shows temperature maps overlaid on magnitude images in coronal plane during 6-focus sonication in rabbit thigh in accordance with the invention. FIG. 12 shows temperature evolution shown for (of the six) foci.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for temperature control in MR-guided administration of ultrasound comprising:
   administering ultrasound therapy to a patient at an in vivo site by emitting focused ultrasound into the site at multiple foci with a multi-focus ultrasound therapy device and by switching the actual focus position to perform a cycled sonication along a time-invariant volumetric pattern;
   monitoring temperature in a localized region of an examination subject in which said site is located during said therapy in real-time by MR thermometry;
   from the MR thermometry, automatically identifying, in a processor, characteristics of a temperature distribution in the monitored region of the examination subject;
   from the computerized processor, implementing temperature control by regulating the ultrasound therapy device by modulating energy deposition at each individual focal point to homogenize a temperature history of all sonicated foci;
   in said processor, implementing a calculation calculating a ratio between energy variation $\delta E_k(n)$ at a time point n and an initial value of energy $E_{K,1}$, in every sonicated focus k among the multiple locations heated simultaneously, without using any a-priori information on tissue properties, according to the following double-branch master equation that takes into account two regimens, respectively before and after reaching a steady state:

$$\frac{\delta E_k(n)}{E_{k,1}} = \begin{cases} w \cdot \min(n, n_{max}) \cdot \left(1 - \frac{T_{k,n}}{\Theta_n}\right) + w \cdot \Omega_{k,n} & \text{if } n \leq n_{switch} \\ -1 + \tanh(\alpha \cdot n_{switch}) + w \cdot \min(n, n_{max}) \cdot \\ \quad \left(1 - \frac{T_{k,n}}{\Theta_{top}}\right) + w \cdot \Omega_{k,n} & \text{if } n > n_{switch} \end{cases}$$

or $$\frac{\delta E_k(n)}{E_{k,1}} = \begin{cases} w \cdot n_{max} \cdot \tanh\left(\frac{n}{n_{max}}\right) \cdot \left(1 - \frac{T_{k,n}}{\Theta_n}\right) + w \cdot \Omega_{k,n} & \text{if } n \leq n_{switch} \\ -1 + \tanh(\alpha \cdot n_{switch}) + w \cdot n_{max} \cdot \tanh\left(\frac{n}{n_{max}}\right) \cdot \\ \quad \left(1 - \frac{T_{k,n}}{\Theta_{top}}\right) + w \cdot \Omega_{k,n} & \text{if } n > n_{switch} \end{cases}$$

wherein tanh is the analytical function hyperbolic tangent, $n_{switch}$ denotes a sampling point where the controller switches irreversibly from the rapid temperature elevation regimen to the steady state regimen, $\alpha$ is a positive number smaller than 0.1, $n_{max}$ is an a-dimentional parameter that limits a maximum strength of the negative reaction, $T_{k,n}$ is the actual temperature at each sonicated focus k for the measurement n, $\Theta_n$ is an average value of measured temperatures $T_{k,n}$ over the sonicated foci for measurement n, $\Theta_{top}$ is a flattop target value of steady state temperature elevation, w is a negative reaction parameter that is a-dimensional and scaled to a square of a temporal resolution, and $\Omega_{k,n}$ is a cumulative relative offset of the measured temperature until the measurement n:

$$\Omega_{k,n} = \begin{cases} \sum_{n'=1}^{n}\left(1 - \frac{T_{k,n'}}{\Theta_{n'}}\right) & \text{if } n \leq n_{switch} \\ \sum_{n'=1}^{n_{switch}}\left(1 - \frac{T_{k,n'}}{\Theta_{n'}}\right) + \sum_{n'=n_{switch}+1}^{n}\left(1 - \frac{T_{k,n'}}{\Theta_{top}}\right) & \text{if } n > n_{switch}. \end{cases}$$

2. A method as claimed in claim 1 comprising a time-dependent negative reaction in the calculation of the delivered energy.

3. A method as claimed in claim 1 comprising selecting a value for negative reaction parameter w in a range between 0.01 divided by the square of the sampling time, and 10.0 divided by the square of the sampling time.

4. A method as claimed in claim 1 comprising implementing said temperature control with the following characteristic differential equation:

$$\frac{d^2\Omega}{dt^2} + w \cdot t \cdot \frac{d\Omega}{dt} + w \cdot \Omega = 0,$$

wherein $\Omega$ designates the integrated offset of temperature at a given focus position.

5. A method as claimed in claim 1 comprising implementing said temperature control with a time domain convergence solution:

$$\Omega(t) \propto \exp\left(-\frac{w \cdot t^2}{2}\right)$$

wherein $\Omega$ designates the integrated offset of temperature at a given focus position.

* * * * *